US011377412B2

(12) United States Patent
Li et al.

(10) Patent No.: US 11,377,412 B2
(45) Date of Patent: Jul. 5, 2022

(54) CATALYST FOR CATALYTIC OXIDATION OF FURFURAL FOR PREPARATION OF MALEIC ACID, PREPARATION METHOD AND USE THEREOF

(71) Applicant: HEFEI ENERGY RESEARCH INSTITUTE, Hefei (CN)

(72) Inventors: Wenzhi Li, Hefei (CN); Tao Yang, Hefei (CN)

(73) Assignee: HEFEI ENERGY RESEARCH INSTITUTE, Hefei (CN)

( * ) Notice: Subject to any disclaimer, the term of this patent is extended or adjusted under 35 U.S.C. 154(b) by 359 days.

(21) Appl. No.: 16/622,941

(22) PCT Filed: Jan. 30, 2019

(86) PCT No.: PCT/CN2019/074023
§ 371 (c)(1),
(2) Date: Dec. 16, 2019

(87) PCT Pub. No.: WO2020/098162
PCT Pub. Date: May 22, 2020

(65) Prior Publication Data
US 2021/0129118 A1 May 6, 2021

(30) Foreign Application Priority Data
Nov. 16, 2018 (CN) .......................... 201811372436.8

(51) Int. Cl.
| | | |
|---|---|---|
| C07C 51/285 | (2006.01) |
| C07C 57/145 | (2006.01) |
| B01J 27/24 | (2006.01) |
| B01J 27/08 | (2006.01) |
| B01J 27/10 | (2006.01) |
| B01J 27/25 | (2006.01) |
| B01J 37/04 | (2006.01) |
| B01J 37/08 | (2006.01) |
| C07C 51/31 | (2006.01) |
| C07C 51/16 | (2006.01) |
| B01J 23/04 | (2006.01) |

(52) U.S. Cl.
CPC ............. *C07C 51/285* (2013.01); *B01J 23/04* (2013.01); *B01J 27/08* (2013.01); *B01J 27/10* (2013.01); *B01J 27/24* (2013.01); *B01J 27/25* (2013.01); *B01J 37/04* (2013.01); *B01J 37/084* (2013.01); *C07C 51/16* (2013.01); *C07C 51/31* (2013.01); *C07C 57/145* (2013.01)

(58) Field of Classification Search
CPC ........ C07C 51/27; C07C 51/31; C07C 51/285; C07C 57/145; B01J 27/08; B01J 27/24; B01J 27/04; B01J 23/04
See application file for complete search history.

(56) References Cited

U.S. PATENT DOCUMENTS

| | | | | |
|---|---|---|---|---|
| 2,421,428 A | * | 6/1947 | Erikr ..................... | C07C 51/313 562/595 |
| 8,609,895 B2 | * | 12/2013 | Saladino ............... | C07C 51/285 562/533 |
| 2021/0402382 A1 | * | 12/2021 | Zhou ....................... | B01J 37/04 |

FOREIGN PATENT DOCUMENTS

| | | | | |
|---|---|---|---|---|
| CN | 103301867 A | 9/2013 | | |
| CN | 106925349 A | 7/2017 | | |
| CN | 107774294 A | 3/2018 | | |
| CN | 108080016 A | 5/2018 | | |
| CN | 108940338 A | * 12/2018 | ............. | B01J 27/24 |
| ES | 2558261 B1 | 11/2016 | | |
| KR | 101743945 | * 6/2017 | ............. | B01J 35/00 |

OTHER PUBLICATIONS

K101743945, Choi, W., et al., Photocatalyst, method for preparing same and method for producing hydrogen peroxide using same, English translation abstract, 1 page (Year: 2017).*
CN108940338 (A), Wang, W., et al., Potassium-doped porous carbon nitride photocatalyst and preparation method thereof, and application, English translation abstract, 1 page (Year: 2018).*
Ning Liangmin, et al., Catalytic conversion of furfural as a biomass-derived platform compound, Petrochemical Technology, Jan. 31, 2017, pp. 130-136.
Qi Wu, et al., Photocatalytic selective oxidation of biomass-derived 5-hydroxymethylfurfural to 2,5 diformylfuran on metal-free g-C3N4 under visible light irradiation, Molecular Catalysis, Apr. 21, 2017, pp. 10-18.

* cited by examiner

*Primary Examiner* — Yate' K Cutliff
(74) *Attorney, Agent, or Firm* — Bayramoglu Law Offices LLC

(57) ABSTRACT

A catalyst for catalytic oxidation of furfural to prepare maleic acid is composed of a carbon nitride doped with a potassium salt. A method for preparing the catalyst includes mixing the potassium salt, a precursor of the carbon nitride and a solvent to obtain a mixture, and drying and calcining the mixture to obtain the catalyst. A use of the catalyst in catalytic oxidation of furfural to prepare maleic acid, wherein the maleic acid is prepared by the step of oxidizing furfural in a solvent in the presence of the catalyst. The invention has the advantages that by using the method provided by the invention to prepare maleic acid, the conversion rate of furfural can be 99% or more and the yield of maleic acid can be up to 70.40%.

11 Claims, No Drawings

CATALYST FOR CATALYTIC OXIDATION OF FURFURAL FOR PREPARATION OF MALEIC ACID, PREPARATION METHOD AND USE THEREOF

CROSS REFERENCE TO THE RELATED APPLICATIONS

This application is the national phase entry of International Application No. PCT/CN2019/074023, filed on Jan. 30, 2019, which is based upon and claims priority to Chinese Patent Application No. 201811372436.8, filed on Nov. 16, 2018, the entire contents of which are incorporated herein by reference.

TECHNICAL FIELD

The present invention relates to the technical field of renewable energy, and more specifically to a catalyst for catalytic oxidation of furfural to prepare maleic acid, the preparation method, and the use thereof.

BACKGROUND

Maleic acid is an important chemical raw material and an intermediate. It is widely used in industry. Maleic acid is mainly used to manufacture unsaturated polyester resin and may also be used as a novel acidulant in the food and beverage industry. A special fruit flavor can be enhanced by adding an appropriate amount of maleic acid, and the taste can be improved. Currently, approximately 1.8 million tons of maleic acid is required worldwide every year. Therefore, efficient production of maleic acid, especially using renewable resources to produce maleic acid, is important and has attracted extensive attention in various countries.

There are many methods for producing maleic acid. However, the main method used in the industry is to oxidize benzene with air at 450-500° C. under the catalytic condition of using vanadium pentoxide as a catalyst, wherein first maleic anhydride is generated and then hydrolyzed to obtain maleic acid. The disadvantages of this method are that fossil fuel products are used, the chemical reaction conditions are extremely harsh, and the chemical reaction has to be performed at a high temperature with high pressure.

At present, producing maleic acid by a method that uses renewable carbon resources instead of fossil fuel products attracts extensive attention worldwide. The method has also achieved accelerated development. However, problems such as low conversion rates of raw materials and low product yield are prevalent in the current research, in regard to producing maleic acid from renewable carbon sources worldwide.

SUMMARY

The present invention aims to solve the problems in the existing methods for preparing maleic acid in the prior art, such as the necessity of using fossil fuel products as raw materials for production, harsh chemical reaction conditions, low conversion rate of raw materials, and low yield of maleic acid.

The present invention solves the above technical problems by the following technical solutions:

The present invention provides a catalyst for catalytic oxidation of furfural to prepare maleic acid, which is composed of a carbon nitride doped with a potassium salt.

Preferably, the potassium salt is one selected from the group consisting of potassium bromide, potassium chloride and potassium nitrate, and a precursor of the carbon nitride is one selected from the group consisting of urea, dicyandiamide and melamine.

Preferably, the mass ratio of the amount of the potassium salt added to the amount of the precursor added is (0.01-0.2):1.

The present invention also provides a method for preparing the above catalyst, including the steps of:

(1) mixing the potassium salt, the precursor of the carbon nitride, and a solvent to obtain a mixture;

(2) drying the mixture from step (1); and (3) calcining the mixture dried in step (2) to obtain the catalyst.

Preferably, the mixing in step (1) is performed at room temperature, stirring the mixture for 6-12 hours. The drying in step (2) is performed at the temperature of 60-120° C. for the drying time of 8-12 hours. The calcining in step (3) is performed at the calcination temperature of 520-550° C. for the calcination time of 2 hours at the heating rate of 1-10° C. per minute using a muffle furnace.

The present invention further provides the use of the above catalyst in catalytic oxidation of furfural to prepare maleic acid. The maleic acid is prepared by subjecting the furfural to catalytic oxidation reaction in a solvent.

Preferably, the oxidation reaction is carried out with an oxidant, the oxidant is one or more selected from the group consisting of hydrogen peroxide, potassium permanganate, potassium chlorate and oxygen.

Preferably, the catalytic oxidation reaction on the furfural is carried out at the temperature of 60-120° C.

Preferably, a mass ratio of the furfural to the catalyst is (1-200):1.

Preferably, a ratio of the volume of the solvent to the mass of the furfural is (1 mL-50 mL):1 mg.

The present invention has the following advantages:

(1) In the present invention, the maleic acid is obtained by directly using furfural as a raw material under mild reaction conditions, thereby avoiding the use of fossil fuel products such as butadiene and benzene, alleviating the pressure of the petroleum industry, and overcoming the shortcomings of traditional chemical synthesis methods and catalytic processes that require harsh reactive conditions. Moreover, the present invention has fewer side reactions, so it is green and non-polluting, which can effectively reduce initial investment costs and facilitate the sustainable development of environmental resources;

(2) By using the catalyst and the preparation method of the present invention for catalytic oxidation of furfural to prepare maleic acid, a relatively high conversion rate of furfural and a relatively high yield of maleic acid can be achieved. The conversion rate of furfural is 99% or more, and the yield of maleic acid is up to 70.40%;

(3) The catalyst prepared in the present invention has a strong catalytic selectivity. It has the characteristics of being recyclable and reusable. In addition, it is easily separated from the products.

DETAILED DESCRIPTION OF THE EMBODIMENTS

The present invention will be further described in detail below with reference to the drawings and examples of the specification.

The test materials, reagents and the like, used in the following examples, are commercially available, unless otherwise specified.

Example 1

A catalyst composed of carbon nitride doped with potassium bromide was prepared by the following steps:
(1) 10 g of urea and 0.5 g of potassium bromide were added to 30 g of water to obtain a mixed solution, the mixed solution was then stirred at room temperature until homogeneous;
(2) The stirred solution in step (1) was dried at 80° C. and then ground into a powder, before placing the powder into a crucible with a lid;
(3) The powder from step (2) was placed in a muffle furnace and calcined at 550° C. for 2 hours, to obtain the catalyst composed of carbon nitride doped with potassium bromide.

The alkalinity of the surface of the carbon nitride doped with potassium bromide prepared in this example was 1.61 mmol/g.

Example 2

A catalyst composed of carbon nitride doped with potassium chloride was prepared by the following steps:
(1) 10 g of urea and 0.5 g of potassium chloride were added to 30 g of water to obtain a mixed solution, the mixed solution was then stirred at room temperature until homogeneous;
(2) The stirred solution in step (1) was dried at 80° C. and then ground into a powder, before placing the powder into a crucible with a lid;
(3) The powder from step (2) was placed in a muffle furnace and calcined at 550° C. for 2 hours, to obtain the catalyst composed of carbon nitride doped with potassium chloride.

Example 3

A catalyst composed of carbon nitride doped with potassium nitrate was prepared by the following steps:
(1) 10 g of urea and 0.5 g of potassium nitrate were added to 30 g of water to obtain a mixed solution, the mixed solution was then stirred at room temperature until homogeneous;
(2) The stirred solution in step (1) was dried at 80° C. and then ground into a powder, before placing the powder into a crucible with a lid;
(3) The powder from step (2) was placed in a muffle furnace and calcined at 550° C. for 2 hours, to obtain the catalyst composed of carbon nitride doped with potassium nitrate.

Example 4

A catalyst composed of carbon nitride was prepared by the following steps:
(1) 10 g of urea was added to 30 g of water to obtain a mixed solution, the mixed solution was then stirred at room temperature until homogeneous;
(2) The stirred solution in step (1) was dried at 80° C. and then ground into a powder, before placing the powder into a crucible with a lid;
(3) The powder from step (2) was placed in a muffle furnace and calcined at 550° C. for 2 hours, to obtain the catalyst composed of carbon nitride.

Example 5

Maleic acid was prepared by catalytic oxidation of furfural with the catalyst of Example 1. The preparation method includes the following steps:

1 mmol of furfural and 50 mg of carbon nitride doped with potassium bromide prepared in Example 1 were added to 4 mL of deionized water to obtain a mixed solution. The mixed solution was then placed in a thick-walled pressure-resistant tube, and then 1 mL of 30% hydrogen peroxide solution was added. After that, a magnetic stirrer was placed in the thick-walled pressure-resistant tube, and the above solution was placed in an oil bath at a rotation speed of 500 rpm, while raising the temperature to 100° C. for 3 hours. Immediately after completion of this process, the thick-walled pressure-resistant tube was taken out and air cooled to room temperature. Subsequently, the compound created from the process was transferred from the reaction vessel and filtered to obtain the filter residue (carbon nitride doped with potassium bromide), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main component of the filtrate was maleic acid with a yield of 70.40%.

After diluting 20 times, the filtrate was measured and analyzed using Waters 515 HPLC (high performance liquid chromatography). The results showed that the conversion rate of furfural in this example was 99% or more.

Example 6

Maleic acid was prepared by catalytic oxidation of furfural with the catalyst prepared in Example 2. The preparation method includes the following steps:

1 mmol of furfural and 50 mg of carbon nitride doped with potassium chloride prepared in Example 2 were added to 4 mL of deionized water to obtain a mixed solution. The mixed solution was then placed in a thick-walled pressure-resistant tube and 1 mL of 30% hydrogen peroxide solution was added. After that, a magnetic stirrer was placed in the thick-walled pressure-resistant tube, and the above solution was placed in an oil bath at the rotation speed of 500 rpm, while raising the temperature to 100° C. for 3 hours. Immediately after completion of the process, the thick-walled pressure-resistant tube was taken out and air cooled to room temperature. Subsequently, the compound created from the process was transferred from the reaction vessel and filtered to obtain the filter residue, which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the components of the filtrate were maleic acid, furanone and succinic acid whose yields were 21.12%, 26.19% and 22.41%, respectively.

After diluting 20 times, the filtrate was measured and analyzed using Waters 515 HPLC (high performance liquid chromatography). The results showed that the conversion rate of furfural in this example was 99% or more.

Example 7

Maleic acid was prepared by catalytic oxidation of furfural with the catalyst of Example 3. The preparation method includes the following steps:

1 mmol of furfural and 50 mg of carbon nitride doped with potassium nitrate prepared in Example 3 were added to 4 mL of deionized water to obtain a mixed solution. The mixed solution was then placed in a thick-walled pressure-resistant tube, and 1 mL of 30% hydrogen peroxide solution was added. After that, a magnetic stirrer was placed in the thick-walled pressure-resistant tube, and then the above solution was placed in an oil bath at the rotation speed of 500 rpm, while raising the temperature to 100° C. for 3 hours. Immediately after completion of the process, the thick-walled pressure-resistant tube was taken out and air cooled to room temperature. Subsequently, the compound created from the process was transferred from the reaction vessel and filtered to obtain filter residue (carbon nitride doped with potassium nitrate), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main components of the filtrate were maleic acid, furanone and succinic acid whose yields were 13.32%, 27.48% and 32.58%, respectively.

After diluting 20 times, the filtrate was measured and analyzed using Waters 515 HPLC (high performance liquid chromatography). The results showed that the conversion rate of furfural in this example was 99% or more.

Example 8

Maleic acid was prepared by catalytic oxidation of furfural with the catalyst of Example 4. The preparation method includes the following steps:

1 mmol of furfural and 50 mg of carbon nitride prepared in Example 4 were added to 4 mL of deionized water to obtain a mixed solution. The mixed solution was then placed in a thick-walled pressure-resistant tube, and 1 mL of 30% hydrogen peroxide solution was added. After that, a magnetic stirrer was placed in the thick-walled pressure-resistant tube, and then the above solution was placed in an oil bath at a rotation speed of 500 rpm, while raising the temperature to 100° C. for 3 hours. Immediately after completion of the process, the thick-walled pressure-resistant tube was taken out and air cooled to room temperature. Subsequently, the compound created from the process was transferred from the reaction vessel and filtered to obtain filter residue (carbon nitride), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main components of the filtrate were maleic acid, furanone and succinic acid whose yields were 16.82%, 27.01% and 24.72%, respectively.

After diluting 20 times, the filtrate was measured and analyzed using Waters 515 HPLC (high performance liquid chromatography). The results showed that the conversion rate of furfural in this example was 99% or more.

Example 9

Maleic acid was prepared by catalytic oxidation of furfural with the catalyst of Example 4. The preparation method includes the following steps:

1 mmol of furfural, 25 mg of carbon nitride prepared in Example 4 and 25 mg of potassium bromide were added to 4 mL of deionized water to obtain a mixed solution. The mixed solution was then placed in a thick-walled pressure-resistant tube, and 1 mL of 30% hydrogen peroxide solution was added. After that, a magnetic stirrer was placed in the thick-walled pressure-resistant tube, and then the above solution was placed in an oil bath at a rotation speed of 500 rpm, while raising the temperature to 100° C. for 3 hours. Immediately after completion of the process, the thick-walled pressure-resistant tube was taken out and air cooled to room temperature. Subsequently, the compound created from the process was transferred from the reaction vessel and filtered to obtain filter residue (carbon nitride), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main component of the filtrate was maleic acid with a yield of 47.31%.

After diluting 20 times, the filtrate was measured and analyzed using Waters 515 HPLC (high performance liquid chromatography). The results showed that the conversion rate of furfural in this example was 99% or more.

Example 10

Maleic acid was prepared by catalytic oxidation of furfural with the catalyst of Example 1. The preparation method includes the following steps:

1 mmol of furfural and 50 mg of carbon nitride doped with potassium bromide prepared in Example 1 were added to 4 mL of deionized water to obtain a mixed solution. The mixed solution was placed in a thick-walled pressure-resistant tube, and then 1 mL of 30% hydrogen peroxide solution was added. After that, a magnetic stirrer was placed in the thick-walled pressure-resistant tube, and then the above solution was placed in an oil bath at a rotation speed of 500 rpm, while raising the temperature to 100° C. for 30 minutes. Immediately after completion of the process, the thick-walled pressure-resistant tube was taken out and air cooled to room temperature. Subsequently, the compound created from the process was transferred from the reaction vessel and filtered to obtain filter residue (carbon nitride doped with potassium bromide), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main component of the filtrate was maleic acid with a yield of 27.32%.

After diluting 20 times, the filtrate was measured and analyzed using Waters 515 HPLC (high performance liquid chromatography). The results showed that the conversion rate of furfural in this example was about 40%.

Example 11

Maleic acid was prepared by catalytic oxidation of furfural with the catalyst of Example 1. The preparation method includes the following steps:

1 mmol of furfural and 50 mg of carbon nitride doped with potassium bromide prepared in Example 1 were added to 4 mL of deionized water to obtain a mixed solution. The mixed solution was placed in a thick-walled pressure-resistant tube, and then 1 mL of 30% hydrogen peroxide solution was added. After that, a magnetic stirrer was placed in the thick-walled pressure-resistant tube, and then the above solution was placed in an oil bath at a rotation speed of 500 rpm, while raising the temperature to 100° C. for 60 minutes. Immediately after completion of the process, the thick-walled pressure-resistant tube was taken out and air cooled to room temperature. Subsequently, the compound created from the chemical reaction was transferred from the reaction vessel and filtered to obtain filter residue (carbon nitride doped with potassium bromide), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main component of the filtrate was maleic acid with a yield of 45.36%.

After diluting 20 times, the filtrate was measured and analyzed using Waters 515 HPLC (high performance liquid chromatography). The results showed that the conversion rate of furfural in this example was about 63%.

Example 12

Maleic acid was prepared by catalytic oxidation of furfural with the catalyst of Example 1. The preparation method includes the following steps:

1 mmol of furfural and 50 mg of carbon nitride doped with potassium bromide prepared in Example 1 were added to 4 mL of deionized water to obtain a mixed solution. The mixed solution was then placed in a thick-walled pressure-resistant tube, and 1 mL of 30% hydrogen peroxide solution was added. After that, a magnetic stirrer was placed in the thick-walled pressure-resistant tube, and then the above solution was placed in an oil bath at a rotation speed of 500 rpm, while raising the temperature to 100° C. for 120 minutes. Immediately after completion of the process, the thick-walled pressure-resistant tube was taken out and air cooled to room temperature. Subsequently, the compound created from the chemical reaction was transferred from the reaction vessel and filtered to obtain filter residue (carbon nitride doped with potassium bromide), which was dried for further use. A portion of the filtrate obtained by the filtration was used to detect the components therein, and another portion was evaporated and recrystallized to give a white solid which was a maleic acid product.

Experimental Results

The components in the above filtrate were detected. The results showed that the main component of the filtrate was maleic acid with a yield of 50.32%.

After diluting 20 times, the filtrate was measured and analyzed using Waters 515 HPLC (high performance liquid chromatography). The results showed that the conversion rate of furfural in this example was about 75%.

Example 13

The recycling performance of carbon nitride doped with potassium bromide was tested.
(1) Primary Recycling Test Maleic acid was prepared in accordance with the preparation method of Example 2, except that the above filter residue was used instead of the carbon nitride doped with potassium bromide used in Example 2 as the catalyst.

Experimental Results

After drying, the filter residue obtained by filtration during the preparation of maleic acid was characterized. As a result, the alkalinity of the surface of the filter residue was 1.52 mmol/g.

The yield of the obtained maleic acid product was detected. As a result, the yield was 60.32% (in the case of primary recycling of the catalyst).
(2) Secondary Recycling Test Maleic acid was prepared under the preparation conditions of the primary recycling test, except that the filter residue obtained in the primary recycling test was used instead of the catalyst used in the primary recycling test.

Experimental Results

The yield of the obtained maleic acid product was detected. As a result, the yield was 55.82% (in the case of secondary recycling of the catalyst).

After diluting 20 times, the filtrate obtained by filtration during the preparation of maleic acid was measured and analyzed using Waters 515 HPLC (high performance liquid chromatograph). The results showed that the conversion rate of furfural in this example was 85%.

The results of the primary and secondary recycling tests show that the catalyst prepared in Example 1 of the present invention has good recycling performance.

The foregoing descriptions are merely preferred embodiments of the present invention. However, the protective scope of the present invention is not limited to the above examples. Various process solutions without substantial difference from the concepts of the present invention should fall within the protective scope of the present invention.

What is claimed is:

1. A method of preparing maleic acid, comprising: performing a catalytic oxidation reaction on furfural using a catalyst in a solvent; wherein the catalyst consists of a carbon nitride doped with a potassium salt.

2. The method according to claim 1, wherein an oxidant used in the catalytic oxidation reaction is one or more compounds selected from the group consisting of hydrogen peroxide, potassium permanganate, potassium chlorate and oxygen.

3. The method according to claim 1, wherein the catalytic oxidation reaction on the furfural is carried out at a temperature of 60-120° C.

4. The method according to claim 1, wherein a mass ratio of the furfural to the catalyst is 1-200:1.

5. The method according to claim 1, wherein a ratio of a volume of the solvent to a mass of the furfural is 1 mL-50 mL:1 mg.

6. The method according to claim 1, wherein the potassium salt is one selected from the group consisting of potassium bromide, potassium chloride and potassium nitrate, and a precursor of the carbon nitride is one selected from the group consisting of urea, dicyandiamide and melamine.

7. The method according to claim 1, wherein a mass ratio of the potassium salt added to a precursor of the carbon nitride added is 0.01-0.2:1.

8. The method according to claim 6, wherein an oxidant used in the catalytic oxidation reaction is one or more compounds selected from the group consisting of hydrogen peroxide, potassium permanganate, potassium chlorate and oxygen.

9. The method according to claim 7, wherein an oxidant used in the catalytic oxidation reaction is one or more compounds selected from the group consisting of hydrogen peroxide, potassium permanganate, potassium chlorate and oxygen.

10. The method according to claim 6, wherein the catalytic oxidation reaction on the furfural is carried out at a temperature of 60-120° C.

11. The method according to claim 7, wherein the catalytic oxidation reaction on the furfural is carried out at a temperature of 60-120° C.

* * * * *